US009249351B2

(12) United States Patent
Dahayanake et al.

(10) Patent No.: US 9,249,351 B2
(45) Date of Patent: *Feb. 2, 2016

(54) VISCOELASTIC SURFACTANT FLUIDS AND RELATED METHODS OF USE

(75) Inventors: Manilal S. Dahayanake, Princeton Junction, NJ (US); Jiang Yang, Plainsboro, NJ (US); Joseph H. Y. Niu, Houston, TX (US); Paul-Joel Derian, Lawrenceville, NJ (US); Ruoxin Li, Plainsboro, NJ (US); David Dino, Cranbury, NJ (US)

(73) Assignee: Rhodia Operations, Aubervilliers (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/975,524

(22) Filed: Dec. 22, 2010

(65) Prior Publication Data

US 2011/0092398 A1    Apr. 21, 2011

Related U.S. Application Data

(63) Continuation of application No. 12/148,742, filed on Apr. 21, 2008, now abandoned, which is a continuation of application No. 10/800,478, filed on Mar. 15, 2004, now abandoned, which is a (Continued)

(51) Int. Cl.
*C09K 8/68* (2006.01)
*A61K 8/02* (2006.01)

(Continued)

(52) U.S. Cl.
CPC ... *C09K 8/68* (2013.01); *A61K 8/02* (2013.01); *A61K 8/368* (2013.01); *A61K 8/40* (2013.01);

(Continued)

(58) Field of Classification Search
CPC ............. A61K 8/02; A61K 8/40; A61K 8/44; A61K 8/46; A61K 8/368; B01F 17/00; B01F 17/0042; C05F 11/00; C05G 3/0064; C09K 8/06; C09K 8/68; C09K 2208/30; C11D 1/04; C11D 1/10; C11D 1/75; C11D 1/83; C11D 1/88; C11D 1/90; C11D 1/143; C11D 1/146; C11D 3/046; C11D 3/2075; C11D 3/3418; C11D 17/003; Y10S 507/922; Y10S 507/924
USPC ................... 516/69, 67, 71, 77, 915; 252/77; 507/922, 924; 510/480, 490, 502, 503
See application file for complete search history.

(56) References Cited

U.S. PATENT DOCUMENTS 3,684,722 A * 8/1972 Hynam et al. ........... 252/187.25
4,122,043 A   10/1978 Kersnar et al.

(Continued)

FOREIGN PATENT DOCUMENTS

DE    3501639    7/1986
EP    0430602    6/1991

(Continued)

OTHER PUBLICATIONS

Kirk Othmer Encyclopedia of Chemical Technology, "Fats and Fatty Oils", G. L. Hasenhuettl as Consultant, © 2005 by John Wiley & Sons, Inc. (Available Online: Feb. 18, 2005), pp. 801-836, obtained Online @ http://mrw.interscience.wiley.com/emrw/9780471238966/search/firstpage (downloaded Jun. 19, 2010).*

(Continued)

*Primary Examiner* — Daniel S Metzmaier

(57) ABSTRACT

Viscoelastic surfactant based aqueous fluid systems useful as thickening agents in various applications, e.g. to suspend particles produced during the excavation of geologic formations. The surfactants are zwitterionic/amphoteric surfactants such as dihydroxyl alkyl glycinate, alkyl ampho acetate or propionate, alkyl betaine, alkyl amidopropyl betaine and alkylimino mono- or di-propionates derived from certain waxes, fats and oils. The thickening agent is used in conjunction with an inorganic water-soluble salt or organic additive such as phthalic acid, salicylic acid or their salts.

9 Claims, 5 Drawing Sheets

Dyanmic shear moduli of different amount of oleamidopropyl betaine (BET-O) in presence of 3% KCl and 0.5% phthalic acid at 25 C.

Related U.S. Application Data continuation of application No. 09/900,229, filed on Jul. 6, 2001, now Pat. No. 6,831,108, which is a continuation of application No. 09/093,131, filed on Jun. 8, 1998, now Pat. No. 6,258,859.

(60) Provisional application No. 60/049,045, filed on Jun. 10, 1997, provisional application No. 60/054,455, filed on Aug. 5, 1997.

(51) Int. Cl.

| A61K 8/368 | (2006.01) |
|---|---|
| A61K 8/40 | (2006.01) |
| A61K 8/44 | (2006.01) |
| A61K 8/46 | (2006.01) |
| A61Q 19/00 | (2006.01) |
| B01F 17/00 | (2006.01) |
| C05F 11/00 | (2006.01) |
| C05G 3/00 | (2006.01) |
| C09K 8/06 | (2006.01) |
| C11D 1/10 | (2006.01) |
| C11D 1/83 | (2006.01) |
| C11D 1/88 | (2006.01) |
| C11D 1/90 | (2006.01) |
| C11D 3/04 | (2006.01) |
| C11D 3/20 | (2006.01) |
| C11D 3/34 | (2006.01) |
| C11D 17/00 | (2006.01) |
| C11D 1/04 | (2006.01) |
| C11D 1/14 | (2006.01) |
| C11D 1/75 | (2006.01) |

(52) U.S. Cl.
CPC ... *A61K 8/44* (2013.01); *A61K 8/46* (2013.01); *A61Q 19/00* (2013.01); *B01F 17/00* (2013.01); *B01F 17/0042* (2013.01); *C05F 11/00* (2013.01); *C05G 3/0064* (2013.01); *C09K 8/06* (2013.01); *C11D 1/10* (2013.01); *C11D 1/83* (2013.01); *C11D 1/88* (2013.01); *C11D 1/90* (2013.01); *C11D 3/046* (2013.01); *C11D 3/2075* (2013.01); *C11D 3/3418* (2013.01); *C11D 17/003* (2013.01); C09K 2208/30 (2013.01); C11D 1/04 (2013.01); C11D 1/143 (2013.01); C11D 1/146 (2013.01); C11D 1/75 (2013.01); Y10S 507/922 (2013.01); Y10S 507/924 (2013.01)

(56) References Cited

U.S. PATENT DOCUMENTS

| 4,243,549 | A | * | 1/1981 | Messenger et al. ............ 516/25 |
|---|---|---|---|---|
| 4,375,421 | A | * | 3/1983 | Rubin et al. ................. 510/403 |
| 4,534,875 | A | * | 8/1985 | Rose ............................. 252/71 |
| 4,615,825 | A | * | 10/1986 | Teot et al. .................... 516/67 |
| 4,889,843 | A | * | 12/1989 | Gazzani ....................... 514/54 |
| 4,900,467 | A | * | 2/1990 | Smith .......................... 510/195 |
| 5,009,799 | A | | 4/1991 | Syrinek et al. |
| 5,069,283 | A | | 12/1991 | Mack |
| 5,143,635 | A | * | 9/1992 | Young et al. ................. 508/518 |
| 5,354,906 | A | * | 10/1994 | Weitemeyer et al. ......... 554/52 |
| 5,512,275 | A | * | 4/1996 | Buck ......................... 424/70.1 |
| 5,551,516 | A | | 9/1996 | Norman et al. |
| 5,607,678 | A | * | 3/1997 | Moore et al. ................. 424/401 |
| 5,610,187 | A | * | 3/1997 | Manning et al. ............. 514/552 |
| 5,700,766 | A | | 12/1997 | Hellsten et al. |
| 5,767,152 | A | * | 6/1998 | Nielsen et al. ................ 514/526 |
| 5,902,784 | A | | 5/1999 | Hellsten et al. |
| 5,965,502 | A | | 10/1999 | Balzer |
| 6,258,859 | B1 | | 7/2001 | Dahayanake et al. |
| 6,482,866 | B1 | | 11/2002 | Dahayanake et al. |
| 6,703,352 | B2 | | 3/2004 | Dahayanake et al. |
| 6,831,108 | B2 | | 12/2004 | Dahanayake et al. |
| 7,279,446 | B2 | * | 10/2007 | Colaco et al. ................. 507/119 |
| 2004/0176478 | A1 | * | 9/2004 | Dahayanake et al. ......... 516/77 |

FOREIGN PATENT DOCUMENTS

| EP | 0342786 | 2/1995 |
|---|---|---|
| EP | 0681832 | 11/1995 |
| JP | 05025057 A * | 2/1993 |
| JP | 05139936 A * | 6/1993 |
| JP | 08073325 A * | 3/1996 |
| WO | 92/14907 | 9/1992 |
| WO | WO 96/28527 | 9/1996 |

OTHER PUBLICATIONS

Kirk Othmer Encyclopedia of Chemical Technology, "Carboxylic Acids, Manufacture", R. W. Johnson and R. W. Daniels, Union Camp Corporation, © 1993 by John Wiley & Sons, Inc. (Article Online Date: Dec. 4, 2000), pp. 1-10 obtained Online @ http://mrw.interscience.wiley.com/emrw/9780471238966/search/firstpage (downloaded Jun. 19, 2010).*

Ullmann's Encyclopedia of Industrial Chemistry, 5th, Completely Revised Ed., vol. A 10: Ethanolamines to Fibers, 4. Synthetic Organic, Edited by Wolfgang Gerhartz et al, copyright 1987, VCH Verlagsgesellschaft mbH, D-6940 Weinheim, Fed. Rep. of Germany, pp. 176-177 and 231-232.*

JPO on EAST, Patent Abstracts of Japan, Japan patent Office, Tokyo, Japan, JP 05139936 A (Jun. 1993), Abstract.*

Derwent Abstract, week 199327, London: Derwent Publications Ltd., AN 1993-216629, JP 05139936 A, (Taisho Pharm Co Ltd), abstract.*

Machine Translation of Publ. No. JP H05-139936, published Jun. 1993, Japan patent Office, Tokyo, Japan, obtained online @ http://dossier1.ipdl.inpit.go.jp/AIPN/odse_top_dn.ipdl?N0000=7400 (Downloaded Feb. 2012).*

Ullmann's Encyclopedia of Industrial Chemistry, $5^{th}$ Ed., vol. A 10, Edited by Gerhartz et al, pp. 176-177 & 231-232, Wiley-VCH Verlag GmbH & Co. KGaA, Weinheim, Germany, (May 5, 1994).*

Machine Translation of Publ. No. JP 08073325 A, published Mar. 1996, Japan patent Office, Tokyo, Japan, obtained online @ http://dossier1.ipdl.inpit.go.jp/AIPN/odse_top_dn.ipdl?N0000=7400 (Downloaded Jun. 10, 2013), pp. 1-11.*

JPO on EAST, Patent Abstracts of Japan, Japan patent Office, Tokyo, Japan, JP 05025057 A (Feb. 1993), Abstract.*

Machine Translation of Publ. No. JP 05-025057 A, published Feb. 1993, Japan patent Office, Tokyo, Japan, obtained online @ http://dossier1.ipdl.inpit.go.jp/AIPN/odse_top_dn.ipdl?N0000=7400 (Downloaded Apr. 5, 2014).*

B. Elvers, et al., "Ullmann's Encyclopedia of Industrial Chemistry," New York, NY, 1990, pp. 5-32 to 5-45.

S.J. Candau, et al., "Rheoligial behaviour of wormlike micelles: effect of salt content," Journal de Physique IV, France, 1993, pp. 197-209, Colloque Cl, supplement au Journal de Physique II, vol. 3, May 1993.

J. G. Weers, et al., "Characterization of viscoelastic surfactant mixtures, Part II: Rheological studies," Colloids and Surfaces, 55, Elsevier Science Publishers B.V., Amsterdam, 1991, pp. 57-72.

"Water, Analysis," Kirk-Othmer Encyclopedia of Chemical Technology, 1998, 18 pp., (Publ. online Dec. 2000).

K. Tsujii, et al., "Addition-Compound Formation between Anionic and Zwitterionic Surfactants in Water," Tochigi Research Laboratories, Tochigi, Japan, 1981, pp. 1437-1441. (The Journal of Physical Chemistry, vol. 86, No. 8, 1982).

T. Iwasaki, et al., "Interactions between Betaine-Type Zwitterionic and Anionic Surfactants in Mixed Micelles," Dept. of Applied Chem. and Industry of Colloid and Interface Science, Science Univ. of Tokyo, Tokyo, Japan, 1190, pp. 30-35. (Langmuir 1991, 7, 30-35).

H. Hoffmann, et al., "The rheological behavouir of different viscoelastic surfactant solutions," Univ. Bayreuth, Bayreuth, Germany, 1994, 12 pp.

(56) References Cited

OTHER PUBLICATIONS

H. Rehage, et al., "Viscoelastic surfactant solutions: model systems for rheological research," Univ. of Bayreuth, Bayreuth, Germany, 1991, pp. 933-973. (Molecular Physics, vol. 74, No. 5, 933-973).

K. Hashimoto, et al., "Rheological Properties of Aqueous Solutions of Alkyl-and Oleyldimethylamine Oxides. Spinnability and Viscoelasticity," Nagoya Univ., Nagoya, Japan, 1991, pp. 1734-1741. (Langmuir 1991, 7, 1734-1741).

H. Hoffmann, et al., "Influence of Ionic Surfactants on the Viscoelastic Properties of Zwitterionic Surfactant Solutions," Univ. of Bayreuth and Institute of Terrestrical Ecology, Bayreuth, Germany and Schlieren, Switzerland, 1992, pp. 2140-2146. (Langmuir 1992, 8, 2140-2146).

Cambridge International Dictionary of English, Cambridge Univ. Press, Cambridge, Great Britain, 1995, p. 1349.

Lang R.F. et al., "Analysis of Ethoxylated Fatty Amines. Comparison of Methods for the Determination of Molecular Weight;" Journal of Surfactants and Detergents, vol. 2, No. 4, Oct. 1999, pp. 503-513.

Kefi, S., et al., "Expanding Applications for Viscoelastic Surfactants (Oilfield Review);" Schlumberger, vol. 16, Issue 4, Winter 2004/2005, pp. 10-22.

First Office Action dated Mar. 3, 2012 corresponding to Chinese Application No. 200910260868.4.

Notification of Second Office Action dated Oct. 18, 2012 corresponding to Chinese Patent Application No. 200910260868.4.

* cited by examiner

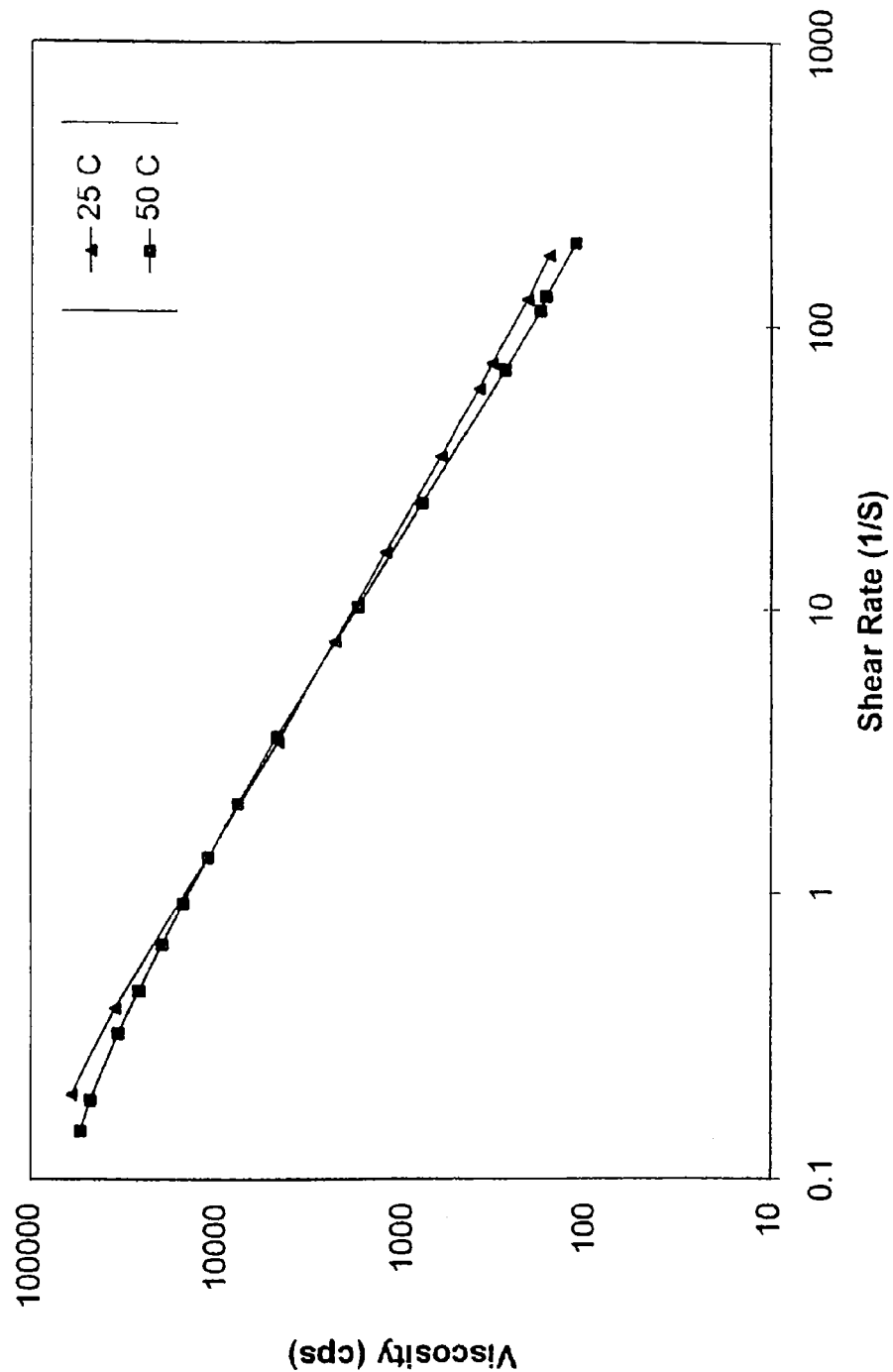
FIG. 1. 5% disodium tallowiminodipropionate with 2.25% phthalic acid at 25 and 50 degree C

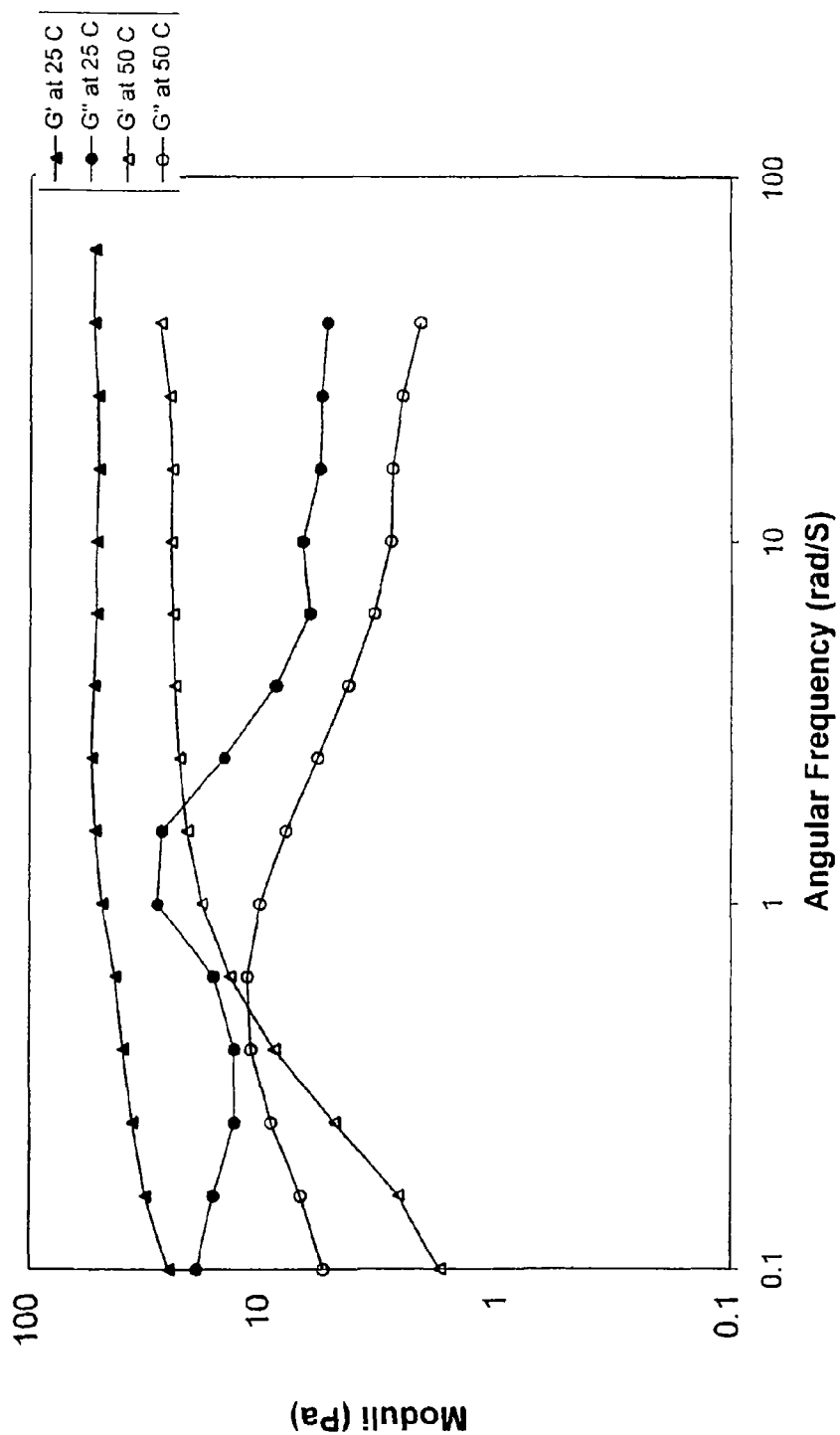
FIG. 2. Dyanmic shear moduli measurements for samples with 5% disodium tallowiminodipropionate and 2.25% phthalic acid at 25 and 50 degree C

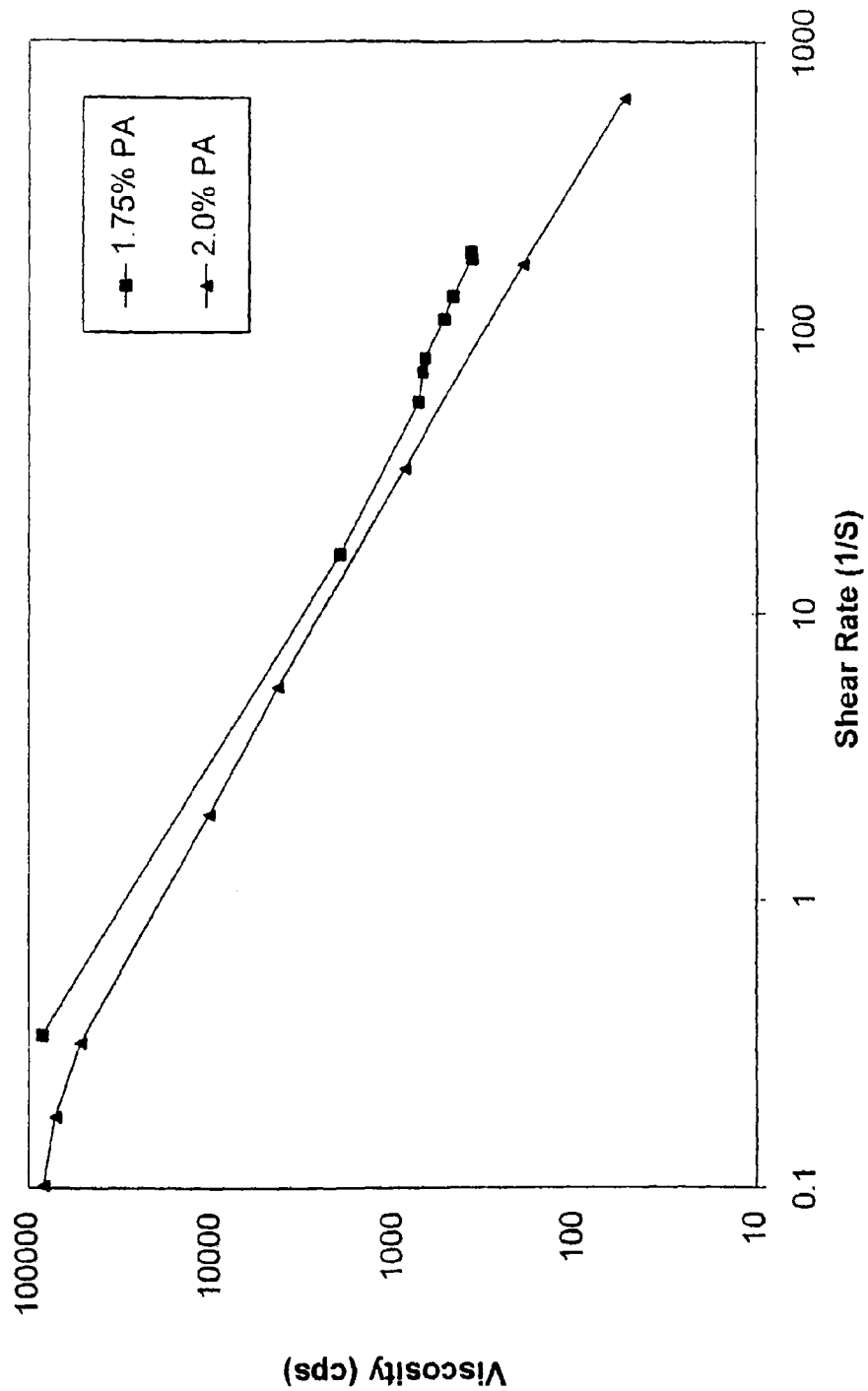
FIG. 3. 5% disodium tallowiminodipropionate, 4% NH4Cl with different amount of phthalic acid (PA) at 25 C

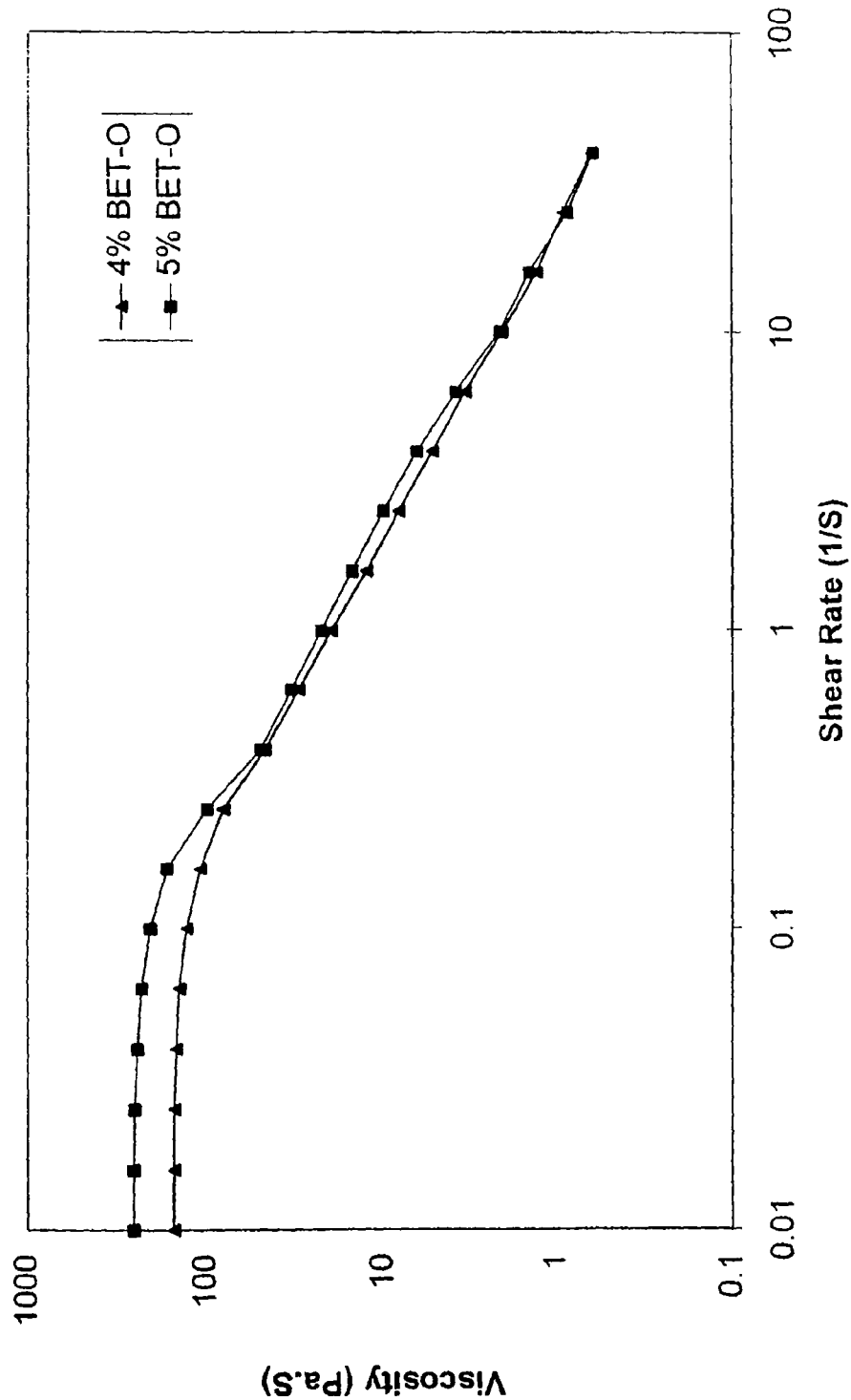
FIG. 4. Steady shear viscosity of different amount of oleamidopropyl betaine (BET-O) in presence of 3% KCl and 0.5% Phthalic Acid at 25 C

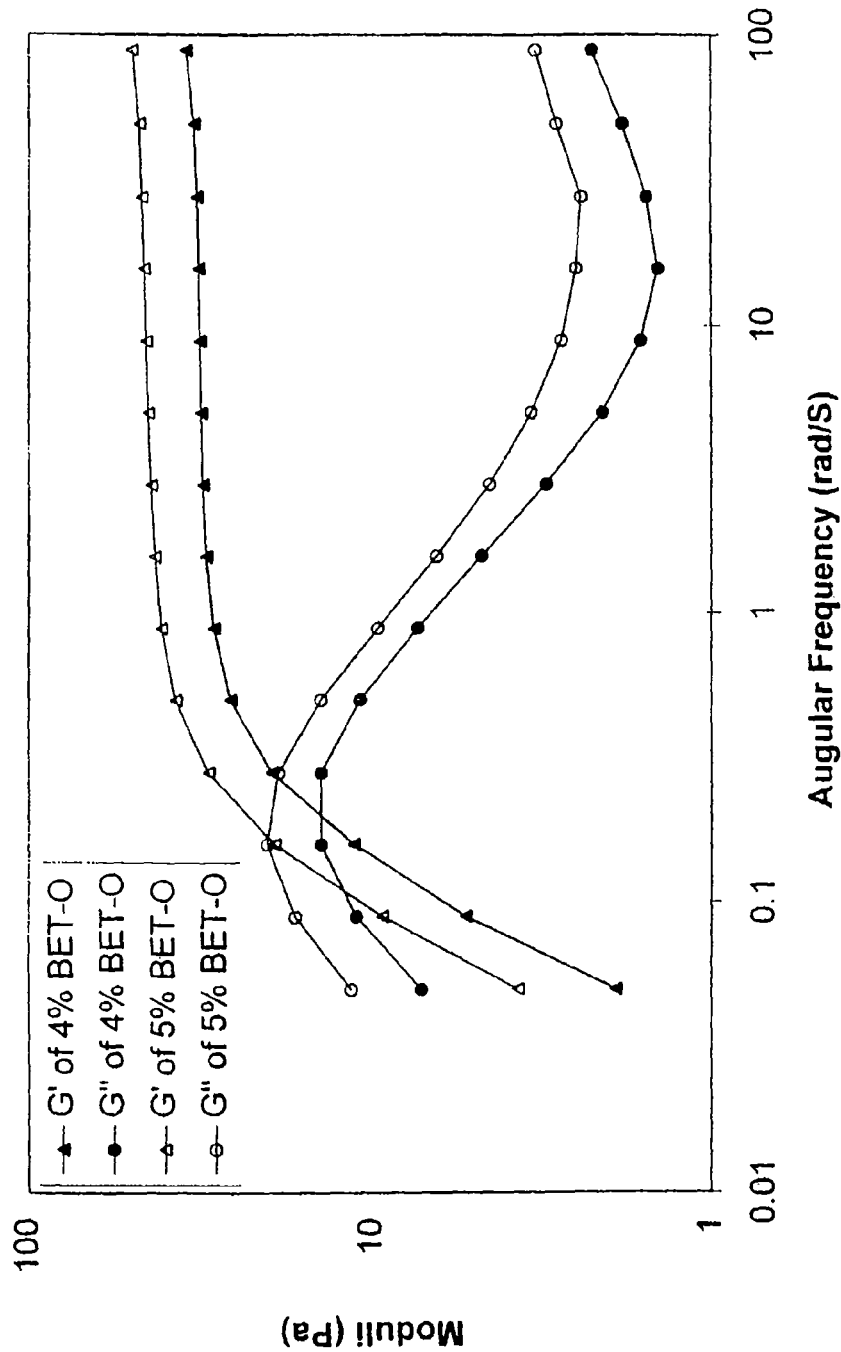
FIG. 5. Dyanmic shear moduli of different amount of oleamidopropyl betaine (BET-O) in presence of 3% KCl and 0.5% phthalic acid at 25 C.

VISCOELASTIC SURFACTANT FLUIDS AND RELATED METHODS OF USE

CROSS REFERENCE TO RELATED APPLICATIONS

This application is a continuation of U.S. Ser. No. 12/148,742, filed Apr. 21, 2008, now abandoned, which is a continuation of U.S. Ser. No. 10/800,478, filed Mar. 15, 2004, now abandoned, which is a continuation of U.S. Ser. No. 09/900,229, filed Jul. 6, 2001, issued as U.S. Pat. No. 6,831,108, which is a continuation application of U.S. Ser. No. 09/093,131, filed Jun. 8, 1998, issued as U.S. Pat. No. 6,258,859, which claims the benefit of the disclosure of U.S. Provisional Patent Application Ser. Nos. 60/049,045, filed Jun. 10, 1997 and 60/054,455, filed on Aug. 5, 1997. The disclosure of U.S. Ser. No. 12/148,742, filed Apr. 21, 2008, and Ser. No. 09/093,131, filed Jun. 8, 1998, are incorporated herein their entireties.

FIELD OF THE INVENTION

This invention relates to viscoelastic fluids which contain a surfactant and to methods of suspending particles using such viscoelastic fluids.

BACKGROUND OF THE INVENTION

It is known to thicken the aqueous phase of a suspension of solid particles or emulsified droplets. The addition of thickeners increases the viscosity of the aqueous phase and thereby retards settling of the particles or droplets. Such retardation is useful to maintain the particles or droplets in suspension during the storage, use, and/or transport of the suspension.

Polymeric thickeners, e.g. starches, which thicken by entanglement of the polymeric chains, have been used to viscosity the aqueous phase of suspensions. Such thickeners can degrade under the influence of mechanical shear or chemical scission (e.g. by oxidation or hydrolysis) of the polymeric chains which results in a loss of viscosity and, thus, suspension stability.

Cationic surfactants have been found which form rod-like micelles under certain conditions. The presence of the rod-like micelles imparts to the fluid viscoelastic properties. However, cationic surfactants tend to have high toxicity and very low biodegradability.

SUMMARY OF THE INVENTION

The present invention provides a viscoelastic fluid useful as a thickener for the suspension of particles. The viscoelastic fluids consist of an amphoteric/zwitterionic surfactant and an organic acid/salt and/or inorganic salts.

Thus, this invention specifically relates to a viscoelastic fluid comprising:

(1) an aqueous medium;

(2) an amount of a surfactant selected from the group consisting of amphoteric surfactants, zwitterionic surfactants, and mixtures thereof, effective to render said aqueous medium viscoelastic; and (3) a member selected from the group consisting of organic acids, organic acid salts, inorganic salts, and combinations of one or more organic acids or organic acid salts with one or more inorganic salts.

In yet another embodiment of the present invention, the invention relates to a viscoelastic fluid consisting essentially of:

(1) an aqueous medium;

(2) an amount of a surfactant comprising an amine oxide surfactant; and (3) an anionic surfactant containing a hydrophobe having at least 14 carbon atoms.

The term "viscoelastic" refers to those viscous fluids having elastic properties, i.e., the liquid at least partially returns to its original form when an applied stress is released. The thickened aqueous viscoelastic fluids are useful as water-based hydraulic fluids in lubricant and hydraulic fracturing fluids to increase permeability in oil production.

The present invention also relates to a method for distributing suspended solid particles such as excavation by-products in a fluid comprised of the viscoelastic fluid of this invention, wherein the solid particles remain suspended for an extended period of time to a side, by transporting the fluid to a site while the solid particles remain suspended in the fluid and depositing the fluid to such site.

This invention also relates to a method for fracturing a subterranean formation comprising pumping the inventive viscoelastic fluid through a wellbore and into a subterranean formation at a pressure sufficient to fracture the formation.

This invention also relates to a detergent formulation comprising a detersive surfactant in admixture with a viscoelastic fluid of this invention.

This invention also relates to the use of the viscoelastic fluid as a drift control agent for agricultural formulations. In this regard, this invention relates to an aqueous formulation of an agricultural chemical and an amount of the viscoelastic fluid of this invention sufficient to increase the average droplet size of a spray of said formulation.

BRIEF DESCRIPTION OF THE FIGURES

FIG. 1 shows viscosity versus shear rate for a viscoelastic surfactant solution prepared by adding 5 percent of disodium tallowiminodipropionate (Mirataine T2C®) and 2.25 percent of phthalic acid to water.

FIG. 2 shows the dynamic modulus G' (storage modulus) and G" (loss modulus) at 25° C. and 50° C. of the same solution as FIG. 1.

FIG. 3 shows the viscosity versus shear rate for a viscoelastic surfactant solution prepared by adding 5 percent of disodium tallowiminodipropionate (Mirataine T2C®), 4 percent of $NH_4Cl$ and 1.75~2.0 percent of phthalic acid to water.

FIG. 4 shows the viscosity versus shear rate for viscoelastic surfactant solutions prepared by adding 4 or 5 percent of disodium oleamidopropyl betaine (Mirataine BET-O®), 3 percent of KCl and 0.5 percent of phthalic acid to water.

FIG. 5 shows the dynamic modulus G' (storage modulus) and G" (loss modulus) at 25° C. and 50° C. of the same solution as FIG. 4.

DETAILED DESCRIPTION OF THE INVENTION

The property of viscoelasticity in general is well known and reference is made to S. Gravsholt, *Journal of Coll. And Interface Sci.*, 57(3), 575 (1976); Hoffmann et al., "Influence of Ionic Surfactants on the Viscoelastic Properties of Zwitterionic Surfactant Solutions", *Langmuir*, 8, 2140-2146 (1992); and Hoffmann et al., The Rheological Behaviour of Different Viscoelastic Surfactant Solutions, *Tenside Surf. Det.*, 31, 389-400, 1994. Of the test methods specified by these references to determine whether a liquid possesses viscoelastic properties, one test which has been found to be useful in determining the viscoelasticity of an aqueous solution consists of swirling the solution and visually observing whether the bubbles created by the swirling recoil after the swirling is stopped. Any recoil of the bubbles indicates viscoelasticity. Another useful test is to measure the storage modulus (G') and the loss modulus (G") at a given temperature. If G'>G" at some point or over some range of points below about 10 rad/sec, typically between about 0.001 to about 10 rad/sec, more typically between about 0.1 and about 10 rad/sec, at a given temperature and if G'>$10^{-2}$ Pascals, preferably $10^{-1}$ Pascals, the fluid is typically considered viscoelastic at that temperature. Rheological measurements such as G' and G" are discussed more fully in "Rheological Measurements", *Encyclopedia of Chemical Technology*, vol. 21, pp. 347-372, (John Wiley & Sons, Inc., N.Y., N.Y., 1997, 4th ed.). To the extent necessary for completion, the above disclosures are expressly incorporated herein by reference.

Viscoelasticity is caused by a different type of micelle formation than the usual spherical micelles formed by most surfactants. Viscoelastic surfactant fluids form worm-like, rod-like or cylindrical micelles in solution. The formation of long, cylindrical micelles creates useful rheological properties. The viscoelastic surfactant solution exhibits shear thinning behavior, and remains stable despite repeated high shear applications. By comparison, the typical polymeric thickener will irreversibly degrade when subjected to high shear.

In the summary of the invention and this detailed description, each numerical value should be read once as modified by the term "about" (unless already expressly so modified), and then read again as not so modified, unless otherwise indicated in context.

The viscoelastic surfactants can be either ionic or nonionic. The present invention comprises an aqueous viscoelastic surfactant based on amphoteric or zwitterionic surfactants. The amphoteric surfactant is a class of surfactant that has both a positively charged moiety and a negatively charged moiety over a certain pH range (e.g. typically slightly acidic), only a negatively charged moiety over a certain pH range (e.g. typically slightly alkaline) and only a positively charged moiety at a different pH range (e.g. typically moderately acidic), while a zwitterionic surfactant has a permanently positively charged moiety in the molecule regardless of pH and a negatively charged moiety at alkaline pH.

The viscoelastic fluid comprises water, surfactant, and a water-soluble compound selected from the group consisting of organic acids, organic acid salts, inorganic salts, and mixtures thereof. Alternatively, the viscoelastic fluid can comprise water, an amine oxide surfactant and an anionic surfactant containing a hydrophobe having at least about 14 carbon atoms. The viscoelastic surfactant solution is useful as a fracturing fluid or water-based hydraulic fluid. The viscoelastic fluid used as a fracturing fluid may optionally contain a gas such as air, nitrogen or carbon dioxide to provide an energized fluid or a foam.

The component of the fluid which will be present in the greatest concentration is water, i.e. typically water will be a major amount by weight of the viscoelastic fluid. Water is typically present in an amount by weight greater than or equal to about 50% by weight of the fluid. The water can be from any source so long as the source contains no contaminants which are incompatible with the other components of the viscoelastic fluid (e.g., by causing undesirable precipitation). Thus, the water need not be potable and may be brackish or contain other materials typical of sources of water found in or near oil fields.

Examples of zwitterionic surfactants useful in the present invention are represented by the formula:

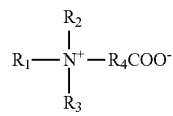

wherein $R_1$ represents a hydrophobic moiety of alkyl, alkylarylalkyl, alkoxyalkyl, alkylaminoalkyl and alkylamidoalkyl, wherein alkyl represents a group that contains from about 12 to about 24 carbon atoms which may be branched or straight chained and which may be saturated or unsaturated. Representative long chain alkyl groups include tetradecyl (myristyl), hexadecyl (cetyl), octadecentyl (oleyl), octadecyl (stearyl), docosenoic (erucyl) and the derivatives of tallow, coco, soya and rapeseed oils. The preferred alkyl and alkenyl groups are alkyl and alkenyl groups having from about 16 to about 22 carbon atoms. Representative of alkylamidoalkyl is alkylamidopropyl with alkyl being as described above.

$R_2$ and $R_3$ are independently an aliphatic chain (i.e. as opposed to aromatic at the atom bonded to the quaternary nitrogen, e.g., alkyl, alkenyl, arylalkyl, hydroxyalkyl, carboxyalkyl, and hydroxyalkyl-polyoxyalkylene, e.g. hydroxyethyl-polyoxyethylene or hydroxypropyl-polyoxypropylene) having from 1 to about 30 atoms, preferably from about 1 to about 20 atoms, more preferably from about 1 to about 10 atoms and most preferably from about 1 to about 6 atoms in which the aliphatic group can be branched or straight chained, saturated or unsaturated. Preferred alkyl chains are methyl, ethyl, preferred arylalkyl is benzyl, and preferred hydroxyalkyls are hydroxyethyl or hydroxypropyl, while preferred carboxyalkyls are acetate and propionate.

$R_4$ is a hydrocarbyl radical (e.g. alkylene) with chain length 1 to 4. Preferred are methylene or ethylene groups.

Specific examples of zwitterionic surfactants include the following structures:

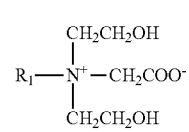

II.

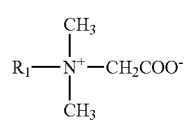

III.

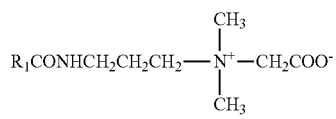

IV.

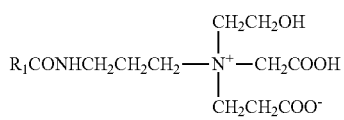

V.

wherein $R_1$ has been previously defined herein.

Examples of amphoteric surfactants include those represented by formula VI:

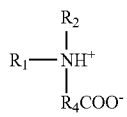
VI.

wherein $R_1$, $R_2$, and $R_4$ are the same as defined above.

Other specific examples of amphoteric surfactants include the following structures:

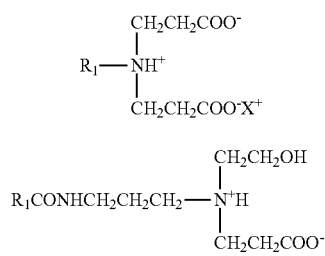
VII.

VIII.

wherein $R_1$ has been previously defined herein, and $X^-$ is an inorganic cation such as $Na^+$, $K^+$, $NH_4^+$ associated with a carboxylate group or hydrogen atom in an acidic medium.

A typical chemical process to synthesize dihydroxy ethoxylate glycinate starting from ethoxylated alkylamine is as follows:

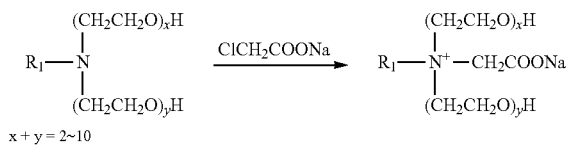

The final products may also include some unreacted starting dihydroxy ethyl alkyl amine, and small amounts of sodium glycolate, diglycolate and sodium chloride as by products. A similar process can be used to prepare propoxylated analogues.

A typical chemical process to synthesize alkyliminiodipropionate from alkyl amine is as follows:

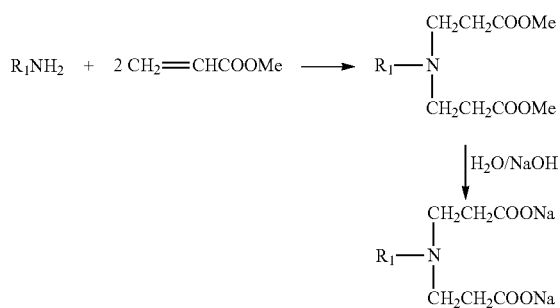

The final products will also include a small amount of methanol, unreacted acrylic acid, alkylamine and some oligomeric acrylate or acid as by products.

A typical chemical process to synthesize alkylamidopropyl betaine from alkyl amine is as follows:

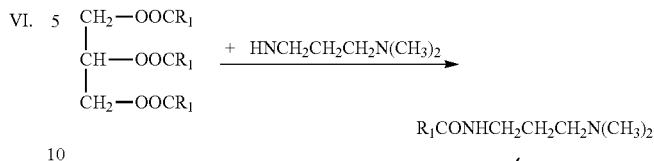

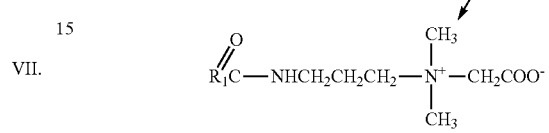

The final products will also include a small amount of sodium glycolate, diglycolate, sodium chloride and glycerine as by products.

In still another embodiment of the invention, the zwitterionic surfactant selected is an amine oxide. This material has the following structure:

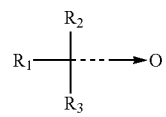

where $R_1$, $R_2$ and $R_3$ are as defined above.

The surfactants are used in an amount which in combination with the other ingredients is sufficient to form a viscoelastic fluid, which amount will typically be a minor amount by weight of the fluid (e.g. less than about 50% by weight). The concentration of surfactant can range from about 0.5% to about 10% percent by weight of the fluid, more typically from about 0.5% to about 8%, and even more typically from about 0.5% to about 6%. Optimum concentrations for any particular set of parameters can be determined experimentally.

The fluid also comprises one or more members from the group of organic acids, organic acid salts, and inorganic salts. Mixtures of the above members are specifically contemplated as falling within the scope of the invention. This member will typically be present in only a minor amount (e.g. less than about 20% by weight of the fluid).

The organic acid is typically a sulfonic acid or a carboxylic acid and the anionic counter-ion of the organic acid salts are typically sulfonates or carboxylates. Representative of such organic molecules include various aromatic sulfonates and carboxylates such as p-toluene sulfonate, naphthalene sulfonate, chlorobenzoic acid, salicylic acid, phthalic acid and the like, where such counter-ions are water-soluble. Most preferred are salicylate, phthalate, p-toluene sulfonate, hydroxynaphthalene carboxylates, e.g. 5-hydroxy-1-naphthoic acid, 6-hydroxy-1-naphthoic acid, 7-hydroxy-1-naphthoic acid, 1-hydroxy-2-naphthoic acid, preferably 3-hydroxy-2-naphthoic acid, 5-hydroxy-2-naphthoic acid, 7-hydroxy-2-naphthoic acid, and 1,3-dihydroxy-2-naphthoic acid and 3,4-dichlorobenzoate. The organic acid or salt thereof typically aids the development of increased viscosity which is characteristic of preferred fluids. Without wishing to be bound by any theory unless expressly noted otherwise in context, it is thought that association of the organic acid or salt thereof with the micelle decreases the aggregation curvature of the micelle and thus promotes the formation of a worm-like or rod-like micelle. The organic acid or salt thereof will typically be present in the viscoelastic fluid at a weight concentration of from about 0.1% to about 10%, more typically from about 0.1% to about 7%, and even more typically from about 0.1% to about 6%.

The inorganic salts that are particularly suitable for use in the viscoelastic fluid include water-soluble potassium, sodium, and ammonium salts, such as potassium chloride and ammonium chloride. Additionally, calcium chloride, calcium bromide and zinc halide salts may also be used. The inorganic salts may aid in the development of increased viscosity which is characteristic of preferred fluids. Further, the inorganic salt may assist in maintaining the stability of a geologic formation to which the fluid is exposed. Formation stability and in particular clay stability (by inhibiting hydration of the clay) is achieved at a concentration level of a few percent by weight and as such the density of fluid is not significantly altered by the presence of the inorganic salt unless fluid density becomes an important consideration, at which point, heavier inorganic salts may be used. The inorganic salt will typically be present in the viscoelastic fluid at a weight concentration of from about 0.1% to about 30%, more typically from about 0.1% to about 10%, and even more typically from about 0.1% to about 8%. Organic salts, e.g. trimethylammonium hydrochloride and tetramethylammonium chloride, may also be useful in addition to, or as a replacement for, the inorganic salts.

As an alternative to the organic salts and inorganic salts, or as a partial substitute therefor, one can use a medium to long chain alcohol (preferably an alkanol), preferably having five to ten carbon atoms, or an alcohol ethoxylate (preferably an alkanol ethoxylate) preferably of a 12 to 16 carbon alcohol and having 1 to 6, preferably 1-4, oxyethylene units.

In the embodiment where the surfactant selected is an amine oxide, it is preferably used in combination with an anionic surfactant containing a hydrophobe having at least about 14 carbon atoms. Examples of suitable anionic surfactants include alkyl sulfates or sulfonates having alkali metal counter ions or alkyl carboxylates, wherein alkyl represents a group that contains from about 14 to about 24 carbon atoms which may be branched or straight chained and which may be saturated or unsaturated, and more preferably contains between about 16 and about 22 carbon atoms.

For this embodiment (amine oxide/anionic surfactant) the weight ratio of the amine oxide to anionic surfactant is from about 100:1 to about 50:50.

In addition to the water-soluble salts and thickening agents described hereinbefore, the viscoelastic fluid used as a hydraulic fracturing fluid may contain other conventional constituents which perform specific desired functions, e.g., corrosion inhibitors, fluid-loss additives and the like. A proppant can be suspended in the fracturing fluid. The pH of the fluid will typically range from strongly acidic (e.g. less than a pH of about 3) to slightly alkaline (e.g. from a pH just greater than 7.0 to about 8.5, more typically to about 8.0) or moderately alkaline (e.g. a pH of about 8.5 to about 9.5). Strongly alkaline pHs (e.g. above a pH of about 10) should be avoided.

It is also conceivable to combine the above amphoteric/zwitterionic surfactants with conventional anionic, nonionic and cationic surfactants to get the desired viscoelastic fluid for a skilled worker. In typical embodiments, the amphoteric/zwitterionic surfactant is typically present in a major amount by weight of all surfactants, and more typically is essentially the only surfactant present. Typically, the viscoelastic fluid will be essentially free of anionic surfactants, e.g. it will contain less than about 0.5%, more typically less than about 0.2%, even more typically less than 0.1% by weight of anionic surfactants.

To prepare the aqueous fluids in accordance with the present invention, the surfactant is added to an aqueous solution in which has been dissolved a water-soluble inorganic salt, e.g. potassium chloride or ammonium chloride and/or at least one organic acid or water-soluble organic acid salt to provide selective control of the loss of particle suspension properties. In the embodiment wherein the fluid is a mixture of water, and amine oxide surfactant and an anionic surfactant, a simple mixture of the three components is utilized. Standard mixing procedures known in the art can be employed since heating of the solution and special agitation conditions are normally not necessary. Of course, if used under conditions of extreme cold such as found in Alaska, normal heating procedures should be employed. It has been found in some instances preferable to dissolve the thickener into a lower molecular weight alcohol prior to mixing it with the aqueous solution. The lower molecular weight alcohol, for instance isopropanol, functions as an aid to solubilize the thickener. Other similar agents may also be employed. Further, a defoaming agent such as a polyglycol may be employed to prevent undesirable foaming during the preparation of the viscoelastic fluid if a foam is not desirable under the conditions of the treatment. If a foam or gas-energized fluid is desired, any gas such as air, nitrogen, carbon dioxide and the like may be added.

The fluid of this invention is particularly useful in the handling of particles generated during the excavation of a geologic formation, e.g. digging, drilling, blasting, dredging, tunneling, and the like, for example in the course of constructing roads, bridges, buildings, mines, tunnels and the like. The particles are mixed with the viscoelastic fluid by means which are effective to disperse the particles in the fluid. The particles generally have a particle size ranging from a fine powder to coarse gravel, e.g. dust, sand, and gravel. Particle size affects the suspendability of excavation processing wastes. For example, small particles suspend better than large particles, and very fine particles suspend so well that the mixture may become too thick to transport by pump or similar means. The distribution of excavation processing waste sizes is also important, as waste which contains particles which span a wide range of sizes is more easily suspended than waste wherein the particles are of about the same size. Therefore, it may be preferred to screen the waste particles prior to applying the present method to scalp off the particles that are too large to suspend to obtain a better particle size distribution.

The viscoelastic fluids of the present invention can be utilized to carry earth or materials excavated during boring, excavating and trenching operations in the deep foundation construction industry, the subterranean construction industry and in tunneling, in well drilling and in other applications of earth support fluids. The ability of the excavation tools or systems to hold and remove increased loading of earth is improved by the suspending properties and lubricating properties of the surfactant viscoelastic fluids.

In one preferred embodiment of this invention, the surfactant can be combined with some fluid-loss control additives known in the industry like water-soluble or water-dispersible polymers (guar and guar derivatives, xanthan, polyacrylamide, starch and starch derivatives, cellulosic derivatives, polyacrylates, polyDADMAC [poly(diallyl dimethyl ammonium chloride] and combinations thereof), clay (Bentonite and attapulgite) in order to give fluid-loss control properties to the excavating fluid and contribute to the stabilization of the wall of the excavation.

More comprehensive information can be found in The University of Houston, Department of Chemical Engineering, Publication No UHCE 93-1 entitled, Effect of Mineral and Polymer slurries on Perimeter Load Transfer in Drilled shafts, published in January 1993, and PCT WO 96/23849, the disclosures of which are incorporated by reference.

The above method for suspending solids has many applications, particularly in mining and the handling of mine tailings. The disclosure of U.S. Pat. No. 5,439,317 (Bishop et al.) is incorporated by reference in this regard. One application is to transport and place mineral processing waste in underground caverns or below grade cavities. Another application is for backfilling of open pits or quarries without the use of costly and labor intensive equipment for deployment. Additionally, the method can be used to place clay or other liners in holding or storage ponds that are used to hold liquids and to prevent the entry of these liquids into the ground water regime and/or to place liners in landfills for a similar purpose. Another application of the method, is for the extinguishing and/or containment of coal mine fires by deploying quantities of solids below ground to seal the fire from sources of oxygen. Still another application of the method is to place solids in previously mined cavities to prevent surface subsidence.

The hydraulic fracturing method of this invention uses otherwise conventional techniques. The disclosure of U.S. Pat. No. 5,551,516 (Norman et al.) is incorporated by reference in this regard. Oil-field applications of various materials are described in "Oil-field Applications", Encyclopedia of Polymer Science and Engineering, vol. 10, pp. 328-366 (John Wiley & Sons, Inc., New York, N.Y., 1987) and references cited therein, the disclosures of which are incorporated herein by reference thereto.

Hydraulic fracturing is a term that has been applied to a variety of methods used to stimulate the production of fluids such as oil, natural gas etc., from subterranean formations. In hydraulic fracturing, a fracturing fluid is injected through a wellbore and against the face of the formation at a pressure and flow rate at least sufficient to overcome the overburden pressure and to initiate and/or extend a fracture(s) into the formation. The fracturing fluid usually carries a proppant such as 20-40 mesh sand, bauxite, glass beads, etc., suspended in the fracturing fluid and transported into a fracture. The proppant then keeps the formation from closing back down upon itself when the pressure is released. The proppant filled fractures provide permeable channels through which the formation fluids can flow to the wellbore and thereafter be withdrawn. Viscoelastic fluids have also been extensively used in gravel pack treatment.

In addition to the applications discussed above, the viscoelastic fluids may also be used as an industrial drift control agent, or as a rheology modifier for personal care formulations (e.g. cleansers, conditioners, etc.) and household cleansers (e.g. detergent formulations). A detergent formulation of the viscoelastic fluids of this invention will further comprise a detersive surfactant. Examples of detersive surfactants and other conventional ingredients of detergent and/or personal care formulations are disclosed in U.S. Ser. No. 08/726,437, filed Oct. 4, 1996, the disclosure of which is incorporated herein by reference.

Typically, the detersive surfactant will be anionic or nonionic. Preferred water-soluble anionic organic surfactants herein include linear alkyl benzene sulfonates containing from about 10 to about 18 carbon atoms in the alkyl group; branched alkyl benzene sulfonates containing from about 10 to about 18 carbon atoms in the alkyl group; the tallow range alkyl sulfates; the coconut range alkyl glyceryl sulfonates; alkyl ether (ethoxylated) sulfates wherein the alkyl moiety contains from about 12 to 18 carbon atoms and wherein the average degree of ethoxylation varies between and 12, especially 3 to 9; the sulfated condensation products of tallow alcohol with from about 3 to 12, especially 6 to 9, moles of ethylene oxide; and olefin sulfonates containing from about 14 to 16 carbon atoms.

Specific preferred anionics for use herein include: the linear $C_{10}$-$C_{14}$ alkyl benzene sulfonates (LAS); the branched $C_{10}$-$C_{14}$ alkyl benzene sulfonates (ABS); the tallow alkyl sulfates, the coconut alkyl glyceryl ether sulfonates; the sulfated condensation products of mixed $C_{10}$-$C_{18}$ tallow alcohols with from about 1 to about 14 moles of ethylene oxide; and the mixtures of higher fatty acids containing from 10 to 18 carbon atoms.

Particularly preferred nonionic surfactants for use in liquid, powder, and gel applications include the condensation product of $C_{10}$ alcohol with 3 moles of ethylene oxide; the condensation product of tallow alcohol with 9 moles of ethylene oxide; the condensation product of coconut alcohol with 5 moles of ethylene oxide; the condensation product of coconut alcohol with 6 moles of ethylene oxide; the condensation product of $C_{12}$ alcohol with 5 moles of ethylene oxide; the condensation product of $C_{12-13}$ alcohol with 6.5 moles of ethylene oxide, and the same condensation product which is stripped so as to remove substantially all lower ethoxylate and non-ethoxylated fractions; the condensation product of $C_{12-13}$ alcohol with 2.3 moles of ethylene oxide, and the same condensation product which is stripped so as to remove substantially all lower ethoxylated and non-ethoxylated fractions; the condensation product of $C_{12-13}$ alcohol with 9 moles of ethylene oxide; the condensation product of $C_{14-15}$ alcohol with 2.25 moles of ethylene oxide; the condensation product of $C_{14-15}$ alcohol with 4 moles of ethylene oxide; the condensation product of $C_{14-15}$ alcohol with 7 moles of ethylene oxide; and the condensation product of $C_{14-15}$ alcohol with 9 moles of ethylene oxide.

Particular detersive applications for which the viscoelastic fluid will be useful include as a thickener for acidic bathroom cleaners, such as those disclosed in U.S. Pat. No. 5,639,722 (Kong et al.) and shower gels such as those disclosed in U.S. Pat. No. 5,607,678 (Moore et al.), the disclosures of which are incorporated by reference. The viscoelastic fluids will also be useful in the manufacture of building products based on plaster, plaster/lime, lime/cement or cement such as those disclosed in U.S. Pat. No. 5,470,383 (Schermann et al.) and foam fluids such as those disclosed in U.S. Pat. No. 5,258,137 (Bonekamp et al.), the disclosures of which are incorporated by reference. In particular, the fluid will be useful for improving the water retention of cement slurries and grouts allowing better pumpability and workability with minimal free water. The fluids will also be useful as thickeners for acidic (e.g. a pH of less than about 5) aqueous slurries of mineral carbonates or oxides, e.g. iron oxide, cerium oxide, silica suspensions, titanium oxide, calcium carbonate, and zirconium oxide. In this regard, the disclosure of U.S. Pat. No. 4,741,781 (De Witte) is incorporated by reference.

The viscoelastic fluid of this invention will also be useful in formulations for the agricultural delivery of solid fertilizers and pesticides such as micronutrients, biologicals, insecticides, herbicides, fungicides, and plant growth regulators. Such formulations are typically aqueous suspensions or solutions comprised of a major amount of water and an agriculturally effective amount of an agriculturally useful chemical. The viscoelastic fluid is typically combined with the other ingredients of the formulation in an amount that effectively reduces the number of droplets below about 150 microns, i.e. the droplets most responsible for drift problems.

The following examples are presented to illustrate the preparation and properties of aqueous viscoelastic surfactant based hydraulic fluids and should not be construed to limit the scope of the invention, unless otherwise expressly indicated in the appended claims. All percentages, concentrations, ratios, parts, etc. are by weight unless otherwise noted or apparent from the context of their use.

EXAMPLES

Example 1

Viscoelastic surfactant solutions are prepared by adding 5 percent of ammonium chloride and 3 to 5 percent of dihydroxyethyl tallow glycinate (Mirataine TM®) to water. The systems were stirred until all of the surfactant dissolved. All of the samples were observed to be viscoelastic by the bubble recoil test. Rheology of solution was measured by Rheometric ARES at 25° C. The results are given below in Table 1.

TABLE 1

| Shear rate | Viscosity (cps) in 5% $NH_4Cl$ | | |
|---|---|---|---|
| ($sec^{-1}$) | 3% Surfactant | 4% Surfactant | 5% Surfactant |
| 10 | 1692.4 | 2619.8 | 3774.7 |
| 18 | 967.7 | 1490.6 | 2144 |
| 32 | 555.5 | 851.6 | 1214.3 |
| 56 | 319.2 | 483.2 | 688.1 |
| 100 | 184.6 | 278 | 393.6 |
| 178 | 107.5 | 159.3 | 225.4 |

Example 2

In a manner similar to Example 1, 0.3 percent of phthalic acid and 2 to 4 percent of dihydroxyethyl tallow glycinate (Mirataine TM®) were put into solution. All of the samples were observed to be viscoelastic by the bubble recoil test. Rheological measurements were performed in the manner described in Example 1 at 25° C. The results are shown below in Table 2:

TABLE 2

| Shear rate | Viscosity (cps) in 0.3% phthalic acid | | |
|---|---|---|---|
| ($sec^{-1}$) | 2% Surfactant | 3% Surfactant | 4% Surfactant |
| 10 | 791.5 | 1474.6 | 1968.7 |
| 18 | 455.3 | 840.9 | 1101.5 |
| 32 | 262.4 | 490 | 564.5 |
| 56 | 152 | 279.2 | 361.7 |
| 100 | 88 | 160.9 | 356.6 |
| 178 | 53 | 91.6 | 342.3 |

Example 3

The rheological measurements were also performed at higher temperatures by FANN Rheometer. The results for 4 percent dihydroxyethyl tallow glycinate (Mirataine TM®) and 0.3 percent of phthalic acid solution are shown below in Table 3:

TABLE 3

| Temperature (° F.) | Viscosity at 100 rpm (cps) |
|---|---|
| 82 | 170 |
| 129 | 51 |
| 189 | 30 |
| 239 | 22 |
| 288 | 15 |

Example 4

The viscoelastic surfactant solutions are prepared by adding 5 percent of disodium tallowiminodipropionate (Mirataine T2C®) and 2.25 percent of phthalic acid to water. The systems were stirred and warmed up to 50° C. until all of the phthalic acid dissolved. All of the samples were observed to be viscoelastic by the bubble recoil test. Rheology was measured for viscosity and dynamic modulus G' (storage modulus) and G" (loss modulus) by a Rheometric SR-200 at 25° C. and 50° C. The results are shown in FIGS. 1 and 2.

Example 5

In a manner similar to Example 4, 5 percent of disodium tallowiminodipropionate (Mirataine T2C®), 4 percent of $NH_4Cl$ and 1.75~2.0 percent of phthalic acid in water were mixed together. All of the samples were observed to be viscoelastic by the bubble recoil test. Rheological measurements were performed in the manner described in Example 4 at 25° C. The results are shown in FIG. 3.

Example 6

The viscoelastic surfactant solutions are prepared by addition of 4.about.5% percent of oleamidopropyl betaine (Mirataine BET-O®), 3% KCl and 0.5% phthalic acid to water. The system was stirred until all phthalic acid dissolved. Rheology was measured for steady viscosity and dynamic modulus G'/G" by Rheometric ARES at 25° C. The results are shown in FIGS. 4 and 5.

Example 7

A viscoelastic surfactant solution is prepared by mixing together in 95.65 parts of water 4 parts of euricic amido propylene dimethyl amine oxide and 0.35 parts of sodium oleyl sulfate. The pH is adjusted to 8 by the addition of NaOH. Its temperature stability is determined by measuring its viscosity in cps (at shear rate of 100 $sec^{-1}$). The results are shown in Table 4.

Example 8

A viscoelastic surfactant solution is prepared by mixing together in 95.50 parts of water 4.0 parts of euricic amido propylene dimethyl amine oxide and 0.50 parts of sodium oleyl sulfate. Its temperature stability is determined by measuring its viscosity in cps (at shear rate of 100 $sec^{-1}$). The results are shown in Table 4.

TABLE 4

| Temperature (° F.) | Viscosity Example 8 | Viscosity Example 7 |
|---|---|---|
| 100 | 282 | 247 |
| 120 | 302 | 293 |

TABLE 4-continued

| Temperature (° F.) | Viscosity Example 8 | Viscosity Example 7 |
|---|---|---|
| 140 | 308 | 305 |
| 160 | 168 | 237 |
| 180 | 162 | 166 |
| 200 | 230 | 231 |
| 220 | 119 | 193 |
| 240 | 50 | 63 |
| 250 | 36 | 36 |
| 260 | 30 | 27 |
| 270 | 16 | 10 |

Example 9

A viscoelastic surfactant-solution is prepared by mixing together in 96.1 parts of water 3.0 parts of euricic amidopropyl amine oxide and 0.9 parts of sodium behenyl sulfate. The pH is adjusted to 9 by the addition of NaOH. Its temperature stability is determined by measuring its viscosity in cps (at shear rate of 100 sec$^{-1}$). The results are shown in Table 5.

Example 10

A viscoelastic surfactant solution is prepared by mixing together in 94.8 parts of water 4.0 parts of euricic amidopropyl amine oxide and 1.2 parts of sodium behenyl sulfate. The pH is adjusted to 9 by the addition of NaOH. Its temperature stability is determined by measuring its viscosity in cps (at shear rate of 100 sec$^{-1}$). The results are shown in Table 5.

TABLE 5

| Temperature (° F.) | Viscosity Example 9 | Viscosity Example 10 |
|---|---|---|
| 100 | 175 | 234 |
| 120 | 168 | 226 |
| 140 | 169 | 297 |
| 160 | 256 | 518 |
| 180 | 309 | 454 |
| 200 | 276 | 173 |
| 220 | 140 | 214 |
| 240 | 154 | 284 |
| 260 | 94 | 351 |

TABLE 5-continued

| Temperature (° F.) | Viscosity Example 9 | Viscosity Example 10 |
|---|---|---|
| 270 | 52 | 215 |
| 280 | 31 | 90 |
| 290 | 25 | 40 |
| 300 | 17 | 4 |

What is claimed is:

1. A viscoelastic fluid, comprising:
   (1) water;
   (2) erucyl amidopropyl betaine present at about 0.5 wt % to about 10 wt % by weight of the fluid; and
   (3) a member, different from erucyl amidopropyl betaine, selected from the group consisting of organic acids, organic acid salts, inorganic salts, a combination of an organic acid with an inorganic salt, and a combination of an organic acid salt with an inorganic salt; wherein the fluid exhibits viscoelasticity, wherein the fluid includes a major amount of water by weight of the fluid, and wherein the fluid includes about 1% to less than about 20% by weight of the member.

2. The fluid of claim 1, wherein erucyl amidopropyl betaine is present at about 0.5 wt % to about 8 wt % by weight of the fluid.

3. The fluid of claim 1, wherein erucyl amidopropyl betaine is present at about 0.5 wt % to about 6 wt % by weight of the fluid.

4. The fluid of claim 1, wherein the member is an inorganic salt and is present at about 1% to about 10% by weight.

5. The fluid of claim 1, wherein the member is an organic acid or salt thereof and is present at about 1% to about 10% by weight.

6. The fluid of claim 5, wherein the organic acid is selected from the group consisting of a sulfonate and a carboxylate.

7. The fluid of claim 1, further comprising a nonionic surfactant or a cationic surfactant.

8. The fluid of claim 1, wherein the member is present at about 1% to about 10% by weight.

9. The fluid of claim 1, wherein erucyl amidopropyl betaine is present at about 0.5 wt % to about 6 wt % by weight of the fluid, wherein the member is present at about 1% to about 10% by weight.

* * * * *